United States Patent
Yoshimura et al.

(10) Patent No.: US 8,658,363 B2
(45) Date of Patent: Feb. 25, 2014

(54) CELL, METHOD, AND ASSAY KIT FOR MEASURING LEVEL OF ARYL HYDROCARBON RECEPTOR TRANSCRIPTIONAL ACTIVATION

(75) Inventors: Seiko Yoshimura, Tokyo (JP); Saeko Uruno, Tokyo (JP); Eiichi Akahoshi, Tokyo (JP); Mitsuko Ishihara, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/430,323

(22) Filed: Mar. 26, 2012

(65) Prior Publication Data
US 2012/0322077 A1 Dec. 20, 2012

Related U.S. Application Data

(63) Continuation of application No. PCT/JP2009/066824, filed on Sep. 28, 2009.

(51) Int. Cl.
*C12Q 1/68* (2006.01)

(52) U.S. Cl.
USPC ............. 435/6.1; 435/368; 435/29; 536/24.1; 536/23.5

(58) Field of Classification Search
None
See application file for complete search history.

(56) References Cited

U.S. PATENT DOCUMENTS

| | | | |
|---|---|---|---|
| 7,811,760 B2 | 10/2010 | Akahoshi et al. | |
| 8,247,643 B2 * | 8/2012 | Akahoshi et al. | 800/14 |
| 2008/0003596 A1 | 1/2008 | Akahoshi et al. | |
| 2010/0132057 A1 | 5/2010 | Akahoshi et al. | |

FOREIGN PATENT DOCUMENTS

| JP | 61-081791 | 4/1986 |
|---|---|---|
| JP | 2002-523050 | 7/2002 |
| JP | 2004-519243 | 7/2004 |
| JP | 2007-60943 | 3/2007 |
| JP | 2007-202555 | 8/2007 |
| JP | 2008-92911 | 4/2008 |

OTHER PUBLICATIONS

Zawada et al., Nature Medicine, vol. 4 (1998) pp. 569-574.*
International Search Report, International Application No. PCT/JP2009/066824, Issued on Oct. 27, 2009.
Eiichi Akaboshi et al., "Shinkei Yurai Saibo o Mochiita Reporter Gene Assay 'TH Assay' (1)"Nippon Kankyo Kagakkai Dai 18 Kai Kankyo Kagaku Toronkai Koen Yoshishu, Jun. 9, 2009, vol. 18 th, p. 60-1.
Mitsuko Kanno et al., "Bioassay ni yoru Kankyo Kagaku Busshitsu no Yugaisei Hyoka Gijutsu", Toshiba Revie, 2008, vol. 63, No. 2 p. 41-4.
Saeko Uruno et al., "Shinkei Yurai Saibo o Mochiita Reporter Gene Assay 'TH Assay' (2)", Nippon Kankyo Kagakukai Dai 18 Kai Kankyo Kagaku Toronkai Koen Yoshishu, Jun. 9, 2009, vol. $18^{th}$, p. 414-5.
Seiko Yoshimura et al., "Dioxin-rui no Shinkei Dokusei o Kenshutsu suru TH assay no Kaihatsu", Dai 9 Kai Kankyo Hormone Gakkai Kenkyu Happyokai Yoshishu, 2006, vol. $9^{th}$, p. 121.
Seiko Yoshimura et al., "Dioxin-rui no Shinkei Dokusei o Kenshutsu suru Reporter Assay (TH Assay) no Kaihatsu", Forum 2006: Pharmaceutical Health Science Environmental Toxicology Koen Yoshishu, 2006, vol. 2006, p. 144.
Saeko Uruno et al., "TH Assay o Mochiita Dioxin-rui no Dokusei Hyoka", Dai 10 Kai Kankyo Hormone Gakkai Kenkyu Happyokai Yoshishu, 2007, vol. $10^{th}$, p. 38.
Alan Poland et al., "2,3,7,8-Tetrachlorodibenzo-p-dioxin and related halogenated aromatic hydrocarbons : examination of the mechanism of toxicity", Ann. Rev. Pharmacol Toxicol, 1982, 22, pp. 517-554.
S.h. Safe, "Comparative toxicology and mechanism of action of polychlorinated dibenzo-p-dioxins and dibenzofurans", Ann.. rev. Pharmacol, Toxicol, 1986, 26, pp. 371-399.
Emily C. Hoffman, et al., "Cloning of a factor required for activity of the Ah(dioxin) receptor", Science, Department of Pathology and Laboratory of Biomedical and Environmental Sciences, University of California, Los Angeles, vol. 252, pp. 954-958, (1991).
Kent G. Golic, "Site-specific recombination between homologous chromosomes in drosophila" Science, Department of Molecular Genetics and Cell Biology, Howard Hughes Medical Institute, University of Chicago, Illinois, vol. 252, pp. 958-959, (1991).
Michael S. Denison, et al., "The DNA recognition site for the dioxin-Ah receptor complex", The Journal of Biological Chemistry, vol. 263, No. 33, Nov. 25, 1998, pp. 17221-17224.
P.M. Garrison, et al., "Species-specific recombinant cell lines as bioassay systems for the detection of 2,3,7,8-tetrachlorodibenzo-p-dioxin-like chemicals", Fundamental and Applied Toxicology 30, 1996, pp. 194-203.
Eiichi Akahoshi, et al., "Over-expression of ahr (aryl hydrocarbon receptor) induces neural differentiation of neuro2a cells: neurotoxicology study", Environmental Health: A Global Access Science Source, 2006, 5:24.

* cited by examiner

*Primary Examiner* — Jim Ketter
(74) *Attorney, Agent, or Firm* — Oblon, Spivak, McClelland, Maier & Neustadt, L.L.P.

(57) ABSTRACT

According to one embodiment, a cell for measuring a level of Ah receptor transcriptional activation is provided. The cell is derived from a neural cell. The cell contains a chromosome into which a reporter construct and an Ah receptor gene are introduced. The reporter construct has a sequence represented by SEQ ID NO: 1 and a reporter gene operably linked to the downstream of the nucleotide sequence. The sequence represented by SEQ ID NO: 1 has a recognizing sequence of an Ah receptor and a nucleotide sequence which is operably linked to the downstream of the recognizing sequence and required to initiate transcription.

7 Claims, 5 Drawing Sheets

CELL, METHOD, AND ASSAY KIT FOR MEASURING LEVEL OF ARYL HYDROCARBON RECEPTOR TRANSCRIPTIONAL ACTIVATION

CROSS REFERENCE TO RELATED APPLICATIONS

This application is a Continuation Application of PCT Application No. PCT/JP2009/066824, filed Sep. 28, 2009, the entire contents of which are incorporated herein by reference.

FIELD

Embodiments described herein relate generally to a method for measuring the level of aryl hydrocarbon receptor transcriptional activation.

BACKGROUND

Dioxin-like substances exhibit their toxicity by binding to the aryl hydrocarbon receptor (hereinafter referred to as "Ah receptor") in a cell (see Ann. Rev. Pharmacol. Toxicol., 22, 517-554 (1982), and Ann. Rev. Pharmacol. Toxicol., 26, 371-399) in the following manner. If dioxin-like substances bind to the Ah receptor, this receptor is activated and translocates into the nucleus. After that, the receptor hetero-dimerizes with an Ah receptor nuclear translocator (hereinafter referred to as an "Arnt"; see Science, 252, 954-958 (1991)). This dioxin-like-substance-binding Ahr/Arnt complex binds to specific promoter element termed dioxin responsive element (DRE) (or xenobiotic responsive element (XRE); see J. Biol. Chem. 263, 17221-17224 (1988)) on a chromosome to activate the transcription of genes located downstream of the responsive element.

One method is disclosed in Fund. Appl. Toxicol., 30, 194-203 (1996). This method is the method for detecting the Ah receptor activation potency of the Lest substance, in which a reporter construct is made by linking a reporter gene, an indicator of Ah receptor activation potency, to the downstream of the responsive element, then the construct obtained thereby is introduced into a cell, and the cell is exposed to a test substance, followed by culturing, to measure the amount of reporter gene expression, thereby detecting the Ah receptor activation potency of the test substance.

Further, the activation of an Ah receptor results in increase in the expression of tyrosine hydroxylase (TH), which is the rate-limiting enzyme of dopamine biosynthesis (see Akahoshi E et al., Environ Health 7; 5; 24 (2006)). Jpn. Pat. Appln. KOKAI Publication No. 2007-202555 discloses a method for measuring the activity of a test substance against the regulatory region of a transcriptional factor having substrate binding ability. This is a method using a cell into which a vector is introduced, wherein a vector contains an enhancer sequence and a promoter sequence inserted into the upstream of luciferase genes, the enhancer sequence including 67 bp responsive sequence of a Ah receptor which mediates induction of the dioxin-responsive gene expression by dioxins and derived from mouse TH genes and the promoter sequence derived from TH genes. The cell used in this method is the one into which vectors are transfected transiently.

In view of this situation, it is desired to develop a method which is reduced in measuring time and enables a wide range of detective sensitivity stably.

DETAILED DESCRIPTION

Figure 1:
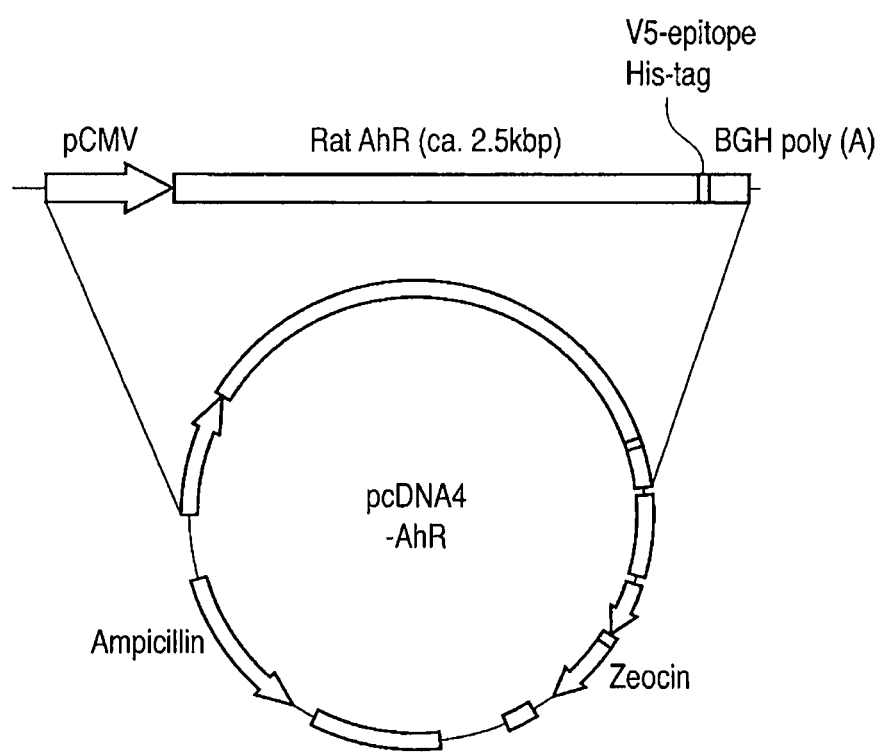
FIG. 1 is a schematic representation of an Ah receptor expression vector.

In general, according to one embodiment, a cell according to the one present embodiment is a recombinant cell produced by carrying out stable transfection to measure the level of transcriptional activation of an Ah receptor.

The cell contains chromosomes into which a reporter construct and an exogenous Ah receptor gene are inserted, which is derived from a neural cell expressing an Arnt gene, wherein the reporter construct is composed of a sequence represented by SEQ ID NO: 1 and a reporter gene, the sequence represented by SEQ ID NO: 1 composed of a responsive sequence of an Ah receptor and a nucleotide sequence which is operatively linked to the downstream of the responsive sequence and required to initiate transcription, and the reporter gene operatively linked to the downstream of the nucleotide sequence.

The recombinant cell may contain chromosomes into which an exogenous Ah receptor gene and an exogenous Arnt gene are inserted. Further, the recombinant cell may contain chromosomes into which an exogenous Ah receptor gene is inserted, if the cell expresses an endogenous Arnt gene. Since the reporter construct and the Ah receptor gene are inserted into a chromosome, these are stably maintained and are stably expressed in the cell. This enables measurement of the level of transcriptional activation of the Ah receptor of even a test substance contained in an extremely low concentration which cannot be conventionally detected. For example, a test substance, for example, 2,3,7,8-TCDD, existing in a concentration of 0.1 pg/ml in a sample may be detected according to the present embodiment.

A cell derived from a neural cell may be used to establish the recombinant cell. The cell derived from a neural cell may be a neuroblastoma cell. The neuroblastoma cell may be a cell derived from any type of species, and preferably a Neuro2a cell derived from a mouse neuroblastoma. As the neuroblastoma cell, an established cell line may be used or a cell isolated from the neuroblastoma may be used.

The responsive sequence of an Ah receptor, which may be an enhancer as will be explained below, is a specific nucleotide sequence on a genome with which a transcriptional factor activated by a substrate is bound. This is a nucleotide sequence having the function of activating the transcription of a gene downstream thereof by binding with the transcriptional factor. An Ah receptor binding enhancer means a nucleotide sequence to which an Ah receptor (namely, a receptor type transcriptional factor) activated by binding with dioxins is bound and which has the function to activate the transcription of a gene downstream thereof by this binding.

Preferable examples of the cell include, though not limited to, cells internationally deposited as FERM BP-11165 and FERM BP-11166 with National Institute of Advanced Industrial Science and Technology International Patent Organism Depositary, AIST Tsukuba Contral 6, 1-1, Higashi 1-chome Tsukuba-shi, Ibaraki-ken 305-8566 Japan, as of Aug. 5, 2009.

Examples of the recombinant cells and a method of establishing the recombinant cell will be explained.

1. Vector

The vector to be transfected into a cell which is to be a material for establishing the recombinant cell will be explained.

(A) Reporter Vector

The reporter vector may be a vector including an enhancer region, a promoter operatively linked to the downstream of the region, and a reporter gene operatively linked to the downstream of the promoter, wherein the enhancer region enhances the transcriptional activity of a gene downstream thereof in response to a test substance in the transcriptional regulatory region of a tyrosine hydroxylase (TH) gene.

The term "operatively linked" means that the linked region is linked so as to exert the function of the region. For example, the description that a promoter and a reporter gene are "operatively linked" means that it is linked such that it exerts promoter activity in a vector to enhance the expression of the reporter gene. In the vector of the present embodiment, the description that a reporter gene is "operatively linked" means that it is linked such that the reporter gene is expressed by the actions of "a region which enhances the transcriptional activity of a gene in response to a test substance having Ah receptor transcriptional activation potency" and a promoter.

(1) Enhancer Region

The enhancer region enhances the transcriptional activity of a gene in response to a material having an Ah receptor transcriptional activation potency. The example of the enhancer region is shown in SEQ ID NO: 2. The enhancer region may be a region containing a region composed of 63 bp which is in the 5' upstream region of a mouse TH gene containing a 25 bp sequence shown in SEQ ID NO: 3 as six tandem repeats sequence. The repeat is not limited to six tandem repeats sequence and may contain an enhancer region in a forward direction (direction: 5'→3') or an enhancer region in a reverse direction (direction: 3'→5'). For example, the repeat sequence may be all composed of enhancer regions in forward directions (direction: 5'→3'), may be all composed of enhancer regions in reverse directions (direction of 3'→5'), or may be a combination of enhancer regions in forward directions (direction: 5'→3') and enhancer regions in reverse directions (direction: 3'→5').

(2) Promoter

The vector necessary to establish the recombinant cell contains, besides the aforementioned enhancer region, a promoter and a reporter gene operably linked to the downstream of the enhancer region.

The promoter may be the core promoter of a TH gene represented by SEQ ID NO: 4 or may be any other promoter if it is a functional, promoter in a host cell. Preferable examples of the promoter include promoters having activity in mammal's cells, for example, an early promoter (SEQ ID NO: 5) of a simian virus (SV40) or SV40 late promoter (SEQ ID NO: 6), human Herpes virus 1 thymidine kinase (TK) promoter (SEQ ID NO: 7), Rous sarcoma virus (RSV) promoter, cytomegalovirus (CMV) promoter (SEQ ID NO: 8) and the like. A person skilled in the art will select a promoter adequate for a host organism.

(3) Reporter Gene

Any reporter known in the technical fields concerned may be used as the reporter gene. The reporter gene is preferably one having such a nature that the activity of its product can be simply measured and the measuring background is lower. Preferable examples of the reporter gene include a luciferase gene, green fluorescent protein gene, β-galactosidase gene, chloramphenicol acetyltransferase gene, and the like. Luminescence, fluorescence, radiation activity, or the like may be utilized corresponding to the type of reporter gene to detect a reporter gene. The reporter gene is a responsive reporter gene which operably exists in a recombinant cell according to the present embodiment and is expressed in the cell when the cell is exposure to substance activating an Ah receptor.

Further, the cell may have chromosomes into which a β-galactosidase gene expressing vector is inserted as an internal standard.

(4) Other Elements

The vector may contain various elements besides the regions described above. For example, a replication origin which functions in adequate organisms and a drug resistant gene may be incorporated into the vector. A drug resistant gene for mammals may be incorporated into the vector to incorporate the vector into a chromosome of a cell and to carry the vector stably. Examples of such a drug resistant gene for mammals include a zeocin resistant gene, G418 resistant gene, and the like. Further, the vector may have an appropriate restriction enzyme recognizing site such as a multi-cloning site.

The vector may have an arbitrary form such as circular plasmid DNA, virus vector DNA and linear DNA fragment.

2. Method for Producing a Vector

A person skilled in the art can produce the vector by using any known method. For example, the vector may be produced in the following manner.

(A) Production of a Reporter Expressing Vector (1) Preparation of a Transcriptional Regulatory Region of a TH Gene The nucleotide sequence of the transcriptional regulatory region of a TH gene has been clarified. This region can be isolated by utilizing, for example, a polymerase chain reaction (PCR). As a nucleic acid which may be used as a template for PCR, for example, a genome DNA extracted from an arbitrary cell may be used.

(2) Production of a Reporter Expression Vector

Then, the transcriptional regulatory region of a TH gene obtained in (1), above, is incorporated into a vector. The production of the vector may be accomplished by linking the transcriptional regulatory region of a TH gene produced in (1), above, in such a manner that the reporter gene functions. The produced reporter expressing vector is preferably sequenced in at least a nucleotide sequence of the transcriptional regulatory region part of a TH gene to confirm that any mutation is not introduced into the nucleotide sequence.

As a vector to be a material for the reporter expressing vector, a commercially available one may be used. For example, a PGV-B2 vector and a PGV-P2 vector (manufactured by Toyo B-Net Co., Ltd.) may be used. In this case, the vector used in the present embodiment is produced only by incorporating the transcriptional regulatory region of a TH gene produced in (1), above, into the commercially available vector.

(B) Production of an Ah Receptor Gene Expression Vector (1) Preparation of an Ah Receptor Gene An Ah receptor gene is prepared. Since its nucleotide sequence has been clarified, the Ah receptor gene can be isolated by utilizing, for example, PCR. Examples of the nucleic acid which may be used as a template for PCR include a cDNA synthesized from a RNA extracted from an arbitrary cell, commercially available cDNA, or the like.

The Ah receptor gene may be a gene derived from any species. Examples of the Ah receptor gene may include genes derived from mammals such as a rat, human or mouse, genes derived from fishes such as a zebra fish or killifish, genes derived from Aves such as a chicken, and the like. The Ah receptor gene is preferably genes derived from mammals, and especially, genes derived from a human. The Ah receptor gene may be either wild type genes which exist naturally or naturally or artificially mutated genes. For example, the mutated gene may be the one a part of which is artificially modified as long as the function of an Ah receptor protein is not changed. Examples of the mutated gene include genes in which one or several nucleotides of an Ah receptor gene are deleted, added and/or replaced. For example, the mutated gene may be the one in which a nucleotide sequence before the translation initiation codon is modified to a Kozak sequence.

(2) Preparation of an Ah Receptor Expression Vector

The above Ah receptor gene is incorporated into an expression vector. Examples of the expression vector include plasmids containing a replication origin which functions in appropriate organisms, a drug resistant gene, and the like. It is preferable that at least one or more types of drug resistant genes be incorporated into the expression vector. Preferable examples of the expression vector include expression vectors having two types of drug resistant genes required for maintaining an expression vector in microorganisms and for the selection of a cell into which a vector is introduced. Examples of the drug resistant gene include a zeocin resistant gene, hygromycin resistant gene, and the like. The plasmid used as the expression vector may be a commercially available one.

For example, an Ah receptor expression vector may be constructed by incorporating the Ah receptor gene prepared in (1), above, into an expression vector having the above characteristics downstream of the promoter in such a manner that the Ah receptor is capable of expressing. Preferable examples of the promoter include promoters that conduct constitutive expression such as a cytomegalovirus (CMV) promoter, Rous sarcoma virus (RSV) promoter and early or late promoter of simian virus (SV40). Inducible promoters such as tetracycline responsive promoters may be used. The promoter may be incorporated in the expression vector in advance or may be incorporated at an appropriate position after the Ah receptor gene is inserted.

The Ah receptor gene may be incorporated into the expression vector in such a manner that it expresses in a natural existent state or that it expresses as a tagged fusion protein. The use of such a tagged protein makes easy to isolate or detect the protein. Examples of the tag to be added include a histidine tag, V5 tag, and the like.

The constructed Ah reporter expressing vector is preferably sequenced in at least the Ah receptor gene part to confirm that any mutation is not introduced into the gene.

(C) β-Galactosidase Gene Expressing Vector

As the β-galactosidase gene expressing vector, pcDNA4/V5-His/LucZ put on the market from Invitrogen Corporation may be used and the β-galactosidase gene expressing vector may be produced by a known method.

3. Introduction of an Expressing Nucleic Acid into Neuroblastoma Cell

Three types of vectors described in (A), (B), and (C), above, that is, the reporter expression vector, Ah receptor expression vector and β-galactosidase gene expression vector are introduced into neuroblastoma cells.

An example of the introduction method is as follows. For example, the cells are seeded in a culture vessel and are cultured in 1:1 mixture medium (DF 1:1) of a Dulbecco-Ham's F12 containing 10% fetal bovine serum. The above three types of vectors are introduced into the cultured cells. As a method of introducing the vector into the cell, any of the methods known by a person skilled in the art, for example, the lipofectamin method, electroporation method, DEAE-dextran method, and calcium phosphate method may be used. For example, Lipofectamine 2000 (manufactured by Invitrogen Corporation) may be used. It is preferable to determine the amount of vector to be introduced, the amount of Lipofectamin 2000 and the number of cells in advance according to a commercially available manual. The vector to be introduced into the cells may be introduced after it is made into a linear form by digestion with a appropriate restriction enzyme.

After the vector is introduced into the cells, the cells containing the vector are cultured for about one day. The cells are detached from the culture vessel and subcultured in a new culture vessel. After the cells are subcultured for one day, an adequate drug is used depending to the drug resistant gene incorporated in the vector to start screening of cell lines. As to the concentration of the drug for screening, an appropriate concentration is determined in advance by a pretest depending to the type of cell to be used. Generally, a concentration at which 80 to 95% of the cells are killed is appropriate as the drug concentration during screening. While changing the medium to a fresh medium containing an appropriate concentration of a drug at a rate of one to two times per week, The culture is continued until the drug resistant colony derived from the cell line into which the vector is introduced is increased to an adequate size. During this time, each vector is inserted into a chromosome and only cells stably carrying each vector on their chromosomes are proliferated and therefore, cells containing a reporter gene which is an expression nucleic acid, Ah receptor gene and β-galactosidase are obtained.

4. Selection of Cells

Cell lines satisfying all requirements (1) to (3), below, are selected from the cells obtained in 3, above. The order of the selection is arbitrarily selected and any of the requirements (1) to (3) may be selected first.

(1) A stably transfected cell with the Ah receptor expression vector is selected from the cells obtained in 3, above. In order to confirm whether or not the cell is stably transfected with the Ah receptor expression vector, it is only required to confirm whether or not the Ah receptor gene is inserted into a cell genome. For example, such a confirmation is performed in the following manner: a DNA detection method which is itself known, such as Southern hybridization; a RNA detection method which is itself known, such as Northern hybridization or reverse transcription-PCR in relation to mRNA transcribed from the Ah receptor gene on the introduced receptor expression vector; or a protein detection method which is itself known such as Western blotting using an antibody specific to an Ah receptor protein about the Ah receptor protein translated from the introduced Ah receptor expression vector. If an Ah receptor protein is expressed in the form of a protein with a tag, a method such as Western blotting using an antibody specific for tag may be used. The confirmation as described above ensures that a stably transfected cell with the Ah receptor expression vector is selected.

(2) The Reporter Gene Functioning when a Cell is in Contact with a Material which Activates the Ah Receptor, that is, a Ligand From the cells obtained in 3, above, a cell in which the reporter gene functions when the cell is in contact with a ligand is selected. The ligand is a material which activates the Ah receptor. As an indication of the selection, the amount of translation product of the reporter gene or an indication value having a correlation with that amount may be measured. Specifically, when a luciferase gene is used as the reporter gene, if luciferin is added to a cell extract from a cell which is brought into contact with the ligand, luminescence occurs at an intensity in proportion to the amount of luciferase in the cell extract. Luciferin is the substrate of luciferase. Therefore, the amount of luciferase, that is, the amount of translation product of the luciferase gene can be found by measuring the intensity of luminescence using a measuring device such as a luminometer.

The selection of cell may be performed by using the amount of expression of the reporter gene as an indicator as follows. A cell obtained in 3, above, is cultured under an Ah receptor ligand-treated and untreated conditions. In the Ah receptor ligand-treated condition, the cell is brought into contact with the Ah receptor ligand. In the untreated condition, the cell are not brought into contact with the Ah receptor ligand. Then the amounts of expression of the reporter gene in the cell are detected in the Ah receptor ligand-treated and untreated conditions, respectively. After that, the amount of expression obtained in the Ah receptor ligand-treated condition is subtracted from the amount of expression obtained in untreated condition to obtain the increased amount of expression of the Ah receptor ligand responsive reporter gene by the contact with the ligand. When the increased amount of expression of the Ah receptor ligand responsive reporter gene is three or more times and preferably five or more times that of the amount of expression in untreated condition, the cell may be selected.

(3) Stably Carrying a β-Galactosidase Expression Vector

A stably transfected cell with a β-galactosidase expression vector is selected from the cells obtained in 3, above. It is only required to confirm whether or not β-galactosidase is inserted into a cell genome to confirm whether or not the cell stably transfected with the β-galactosidase gene expression vector. This confirmation may be performed by the following procedures: for example, a DNA detection method which is itself known, such as Southern hybridization; a RNA detection method which is itself known, such as Northern hybridization or reverse transcription-PCR in relation to mRNA transcribed from β-galactosidase gene carried on the introduced β-galactosidase gene expression vector; or a protein detection method, which is itself known, by using β-galactosidase translated from the introduced β-galactosidase gene expression vector. Further, because β-galactosidase has an enzymatic activity, it may be brought into contact with a substrate specific to the protein to measure the amount of reaction with the substrate by using absorbance as an index.

5. Method of Evaluating a Test Substance by a Recombinant Cell

Using the recombinant cell obtained above according to the present embodiment, the Ah receptor transcriptional activation potency of the test substance can be assayed in the following manner.

Step 1: Step of Bringing a Test Substance into Contact with the Recombinant Cell.

If the contact between the recombinant cell according to the present embodiment and the test substance is kept, for example, for about 24 hours or more, the amount of translation product of the reporter gene almost reaches saturation. Therefore, the generation of measuring errors caused by a measuring time deviation and the like can be limited. The contact between the cell and the test substance is preferably kept over about 6 hours or more, 12 hours or more, about 24 hours or less, or about 24 hours or more to limit the generation of measuring errors.

An example of more specific embodiments is as follows. The recombinant cell is seeded on a 24-well plate with about $8\times10^4$ cells per well and 500 μL of 1:1 mixture medium (DF 1:1) of a Dulbecco-Ham's F12 containing 10% fetal bovine serum is added. The cells are cultured at 37° C. for several hours to one day under the condition of a saturated humidity and 5% $CO_2$. A solution containing the test substance is added to a medium containing the recombinant cells under culturing. Alternatively, for the culturing system containing the medium and the recombinant cells, the medium may be replaced with a medium containing the test substance. Examples of the solvent used to dissolve the test substance include dimethylsulfoxide (DMSO), ethanol, distilled water, and the like. In order to reduce the influence of the solvent on the recombinant cell, the proportion by volume of the test substance solution to be added to the medium is preferably about 0.5% (v/v) to about 1% (v/v) or less of the volume of the medium. When the solution of the test substance is an aqueous solution, for example, the solution may be added to the above medium after it is filtered using a filter having a pore size of 22 μm and sterilized.

Step 2: Measurement of the Amount of Translation Product of the Reporter Gene or an Indication Value With regard to the recombinant cell brought into contact with the test substance in the above manner, the amount of translation product of the reporter gene or an indication value having a correlation to that amount is measured.

When an Ah receptor expressed by the recombinant cell is activated by binding with a test substance (for example, dioxin-like substances), the transcription of the reporter gene is promoted, and a reporter protein is accumulated in the recombinant cell. Here, the reporter protein is a translation product of the reporter gene. The amount of translation product of the reporter gene per cell in the recombinant cell or an indication value having a correlation to that amount per cell in the recombinant cell may be measured by measuring the amount of reporter protein or an indication value having a correlation to that amount.

An example of specific embodiments is as follows. When a luciferase gene is used as the reporter gene, luciferin may be added to a cell extract from the recombinant cell made to be in contact with a test substance to measure the intensity of luminescence. This luminescence varies in proportion to the amount of luciferase in the cell extract. Therefore, if the intensity of luminance is measured by a measuring device such as a luminometer, the amount of produced luciferase, that is, the amount of translation product of the luciferase gene is clarified.

Step 3: Assessment of the Ah Receptor Transcriptional Activation Potency of a Test Substance The Ah receptor transcriptional activation potency of a test substance is assayed based on the amount of translation product or an indication value having a correlation to that amount obtained in step 2, above. Examples of the Ah receptor transcriptional activation potency include, for example, agonist activity against an Ah receptor or antagonist activity against an Ah receptor.

In one embodiment, an assay of the Ah receptor transcriptional activation potency may be made as follows. The cell is cultured under a test substance-treated condition and a untreated condition. In the test substance-treated condition, the stable transfectant brought into contact with the test substance. In the untreated condition, the stable transfectant not brought into contact with the test substance. After the contact for a predetermined amount of time, the amount of translation product of the reporter gene is measured in the stable transfectant in each of the test substance-treated condition and untreated condition. After that, the amount of translation product measured in the test substance-treated condition and that measured in the untreated condition may be compared each other. Here, the amount of translation product measured in the untreated region can be used as a reference value. Based on this result, the test substance may be estimated for the Ah receptor transcriptional activation potency.

For example, when the amount of translation product of the reporter gene obtained in the test substance-treated condition is higher than the reference value, the test substance may be estimated to have agonist activity against the Ah receptor.

In the same manner as the amount of translation product is measured, based on an indication value having a correlation to the amount of translation product from each of the test substance-treated condition and untreated region, the estimation can be accomplished for a test substance.

Alternatively, an assay of the Ah receptor transcriptional activation potency may be made as follows. The cell is cultured under a test substance-treated condition and a untreated condition. In this case, in the test substance-treated condition, the recombinant cell is brought into contact with a dioxin-like active substance such as TCDD and a test substance at the same time. And in the untreated condition, the recombinant cell is brought into contact with the dioxin-like active substance but is not brought into contact with the test substance. After the contact for a predetermined amount of time, the amount of translation product of the reporter gene is measured in the recombinant cell in each of the test substance-treated condition and untreated condition. When the amount of translation product of the reporter gene in the test substance-treated condition is lower than the amount of translation product of the reporter gene in the untreated condition, the test substance may be estimated to have antagonist activity against the Ah receptor.

In the same manner as the amount of translation product is measured, based on an indication value having a correlation to the amount of translation product from each of the test substance-treated condition and untreated condition, the estimation can be accomplished for a test substance to have antagonist activity against the Ah receptor.

Moreover, based on the agonist activity of the test substance against the Ah receptor which is assayed by the above assay method as mentioned above, the amount of test substance may be converted to the amount of TCDD by calculating. For example, TCDD is added as a test substance to the above measurement system by varying its concentration step by step to measure the amount of translation product of the reporter gene in each concentration or an indication value having a correlation to that amount. Then, the obtained measured values and the concentrations of TCDD are plotted to make a standard curve. The amount of translation product of the reporter gene measured for various test substances or an indication value having a correlation to that amount may be applied to the standard curve to calculate the amount of test substance in terms of TCDD. The calculated amount in terms of TODD has the same meaning as "toxic equivalent (TEQ)" in the dioxins analysis method in GC-MS measurement.

6. Selecting or Screening Method

A material having Ah receptor transcriptional activity can be selected and/or screened based on the Ah receptor transcriptional activation potency evaluated in the above evaluation method.

The selecting and/or screening method is required to involve a step of selecting and/or screening a material having an Ah receptor transcriptional activation potency based on the Ah receptor transcriptional activation potency evaluated by a method carried out according to the method described in (5), above. For example, each arbitrary threshold value may be determined in advance with respect to the amount of translation product of the reporter gene, an indication value having a correlation to that amount, or the amount obtained by the values in terms of TCDD. On the other hand, for a material or materials included in a subject material group to be evaluated, the Ah receptor transcriptional activation potency is evaluated by a method carried out according to the method described in (5), above. Based on the resulting data and the predetermined threshold value, a specified material is selected or deleted from the subject material group. In particular, in the case that the measured amount or value for the material is higher or lower than the threshold value, the specified subject material may be selected or deleted from the subject material group. This selecting or screening method is also one embodiment of the present application.

7. Assay Kit

Moreover, as one embodiment, there is provided an assay kit for carrying out either the aforementioned method of assaying the Ah receptor transcriptional activation potency which a test substance has or the aforementioned method of selecting or screening a material having an Ah receptor transcriptional activation potency.

This assay kit may contain at least a recombinant cell defined herein. Further, this assay kit may be provided with, though not limited to, one or more selected from the group composed of the aforementioned recombinant cell defined herein, a cell for producing the recombinant cell, various vectors giving intended genes to the cell, a medium, a reagent for carrying out this assaying method, a reagent for making a standard curve, a cell extracting reagent, a standard product, cell detachment enzyme such as trypsin, an antibiotic substance, a culture vessel for culturing a cell there, a reactor for performing a reaction there, an instruction manual, and the like.

EXAMPLES

Example 1

Preparation of an Ah Receptor Gene

All RNAs were extracted from a rat brain by using an RNeasy kit (manufactured by Qiagen). The extracted RNA was reversely transcribed by using an oligo (dT)-primer. Then, using this transcribed RNA as a template, Pyrobest DNA polymerase was used to undergo a PCR reaction including denaturing: 94° C., one minute, annealing: 55° C., one minute, and extension: 72° C., four minutes in one cycle, repeating this cycle 25 times, to amplify the coding region of the rat Ah receptor gene.

As the primer, the following ones were used;

a forward primer:
(SEQ ID NO: 9)
5'-CCCAAgCTTACCATGAgCAgCggCgCCAACATCA a reverse primer:
(SEQ ID NO: 10)
5'-CCgCTCgAgAggAATCCgCTgggTgTgATATCAg.

A HindIII recognition sequence was added to the 5'-terminal of the forward primer and an XhoI recognition sequence was added to the 5'-terminal of the reverse primer. Further, the reverse primer was so designed that the Ah receptor protein was expressed as a fusion protein with a V5 epitope and a His-tag.

Example 2

Preparation of a Receptor Expression Vector into which an Ah Receptor Gene is Incorporated As the expression vector, pcDNA4/V5-His B (manufactured by Invitrogen Corporation) was used. In this pcDNA4/V5-His B, a multi-cloning site (MCS) is positioned between a cytomegalovirus (CMV) promoter sequence and a V5 epitope sequence. A target protein can be excessively expressed under the control of a CMV promoter by incorporating a sequence encoding a desired gene into an appropriate restriction enzyme region in MCS.

Further, a V5 epitope and a histidine tag can be added to the C-terminal of a target protein by appropriately changing the 3'-terminal of the coding sequence of the gene to be incorporated. First, the coding region of the rat Ah receptor gene which amplified this expression vector in Example 1 was digested with a restriction enzyme HindIII and XhoI. Similarly, pcDNA4/V5-His B was digested with HindIII and XhoI. Then, pcDNA4/V5-His B was linked with the coding region of the rat Ah receptor gene to thereby produce an expression vector pcDNA4-rAhR (FIG. 1). pcDNA4-rAhR was introduced into *Escherichia coli* TOP10 (manufactured by Invitrogen Corporation) to amplify and maintain.

In the produced pcDNA4-rAhR, the coding region of the rat Ah receptor gene was sequenced to confirm that a variant was not introduced into that region. As the primer for sequencing, a T7 primer and a BGH reverse primer were used.

Example 3

Production of a Reporter Vector pTHEn-Luc Containing an Ah Receptor Responsive Reporter Gene A single-stranded DNA was synthesized which is obtained by repeating the 5'-upstream side-175 bp to −237 bp of a TH gene coding region containing a sequence described in SEQ ID NO: 3 twice. This DNA was used as a template to prepare a double-stranded DNA by PCR. The sequence of one of the single-stranded DNAs contained in the above double-stranded DNA and the nucleotide sequence of the used PCR primer are shown below. This single-stranded DNA was used as a template.

Single-stranded DNA (forward):
(SEQ ID NO: 11)
5'-GCCAGCCCCTGTCTTCATGTCGTGTCTAGGGCGGAGGGTGATTCAGA

GGCAGTGCCTGCGACAGTGGATGCAGTCTTCATGTCGTGTCTAGGGCGGA

GGGTGATTCAGAGGCAGGTGCCTGCGACAGTGGATGCAATTAGATCTA-3'

Primer (forward):
(SEQ ID NO: 12)
5'-GCCAGCCCCTGTCTTC-3'

Primer (reverse):
(SEQ ID NO: 13)
5'-TAGATCTAATTGCATC-3'

The DNAs of the double-stranded DNA obtained by PCR were phosphorylated by T4-polynucleotidekinase, then they were ligated to each other by T4-DNA ligase. Then a DNA fragment having three links was separated by agarose gel electrophoresis and the DNA fragment was purified by a QIAquick gel extraction kit (Qiagen). The purified DNA fragment was a fragment obtained by repeating a TCDD responsive enhancer six times. This DNA was incorporated into a PGV-P2 vector (Toyo B-Net Co., Ltd.) which was a luciferase expression vector. First, a SV40 promoter on PGV-P2 was removed by digesting with a restriction enzyme HindIII and Xho I and recombined with the core promoter of the TH gene (the region from the transcriptional start site [0 bpo] to 5' upstream-100 bp, [SEQ ID NO: 4]) to produce a vector (PGV-THp). PGV-THp was digested with Sma I, into which a DNA sequence (SEQ ID NO: 2) composed of six repeated TCDD responsive enhancers was then integrated to produce a reporter vector construct pTHEn-Luc.

The TCDD responsive enhancer nucleotide sequence and TH gene core promoter sequence on pTHEn-Luc were confirmed by sequencing.

In order to introduce a zeocin resistant gene into the produced vector pTHEn-Luc, a pcDNA4-rAhR vector was used as a template and the following primers were used to obtain 790 bp PCR product containing the zeocin resistant gene and its expression promoter:

forward primer:
(SEQ ID NO: 14)
5'-CGGAGCGCTCCTAGGCTTTTGCAAAAAGCTCCCG-3';
and reverse primer:
(SEQ ID NO: 15)
5'-GCTCGCGACGGTATACAGACATGATAAGATACAT-3'.

The amplified PCR product was purified by a QIAquick PCR Purification kit (manufactured by Qiagen).

The purified PCR product and pTHEn-Luc vector were respectively digested with Aor51HI. Then, the PCR product was purified by a QIAquick PCR Purification kit (Qiagen). The purified PCR product was subjected to dephosphorylation treatment by using BAP (manufactured by Takara Bio Inc.).

Figure 2:
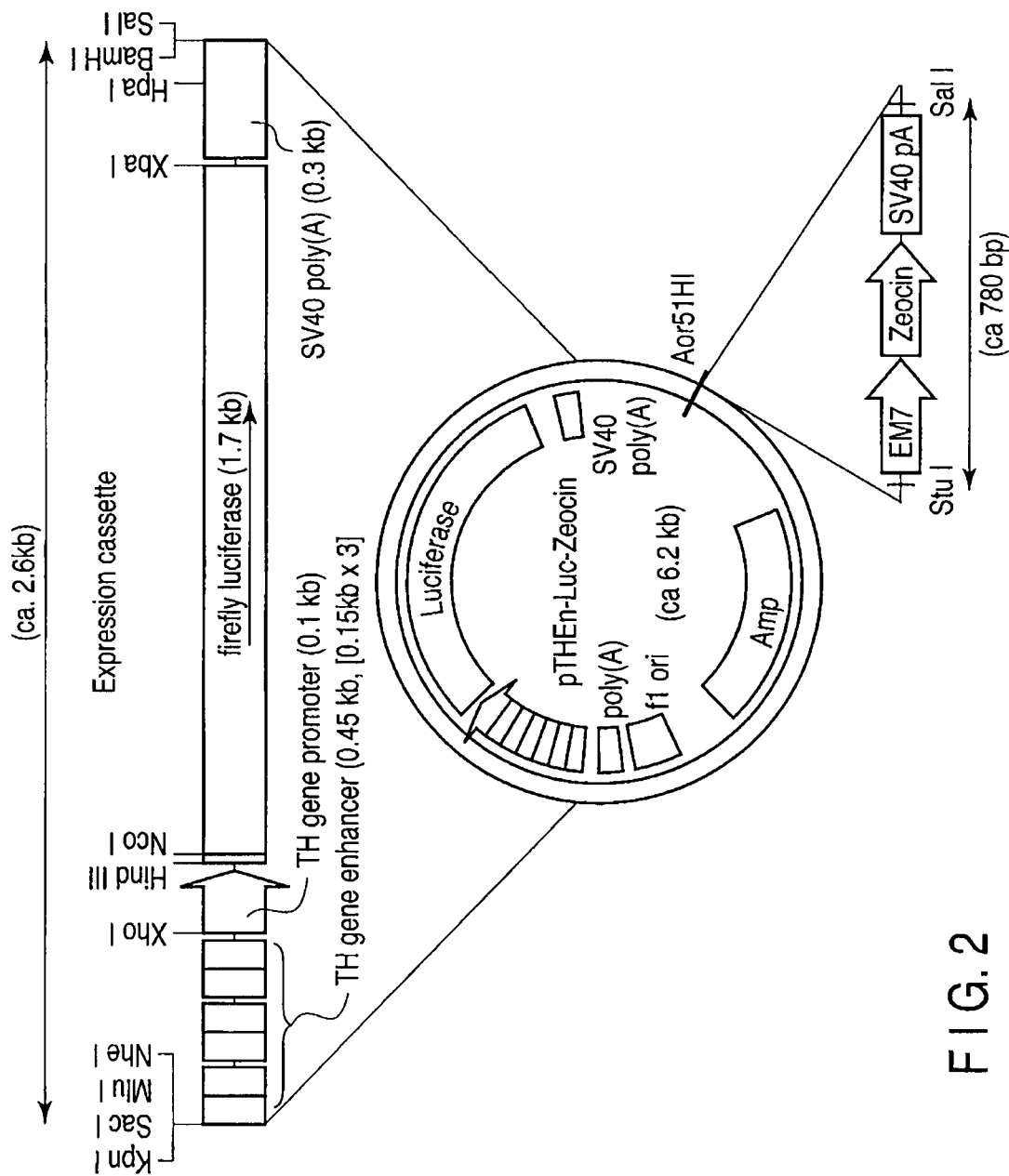
FIG. 2 is a schematic representation of a pTHEn-Luc-Zeocin promoter vector, which contains an Ah receptor responsive reporter gene.

The pTHEn-Luc vector after the enzymatic digestion was subjected to agarose electrophoresis, cut out from the gel based on its molecular weight, and purified by a QIAquick Gel Extraction Kit. The dephosphorylated PCR product was linked to the obtained single-stranded pTHE-Luc vector to construct a pTHEn-Luc-Zeocin vector having a zeocin resistant function (FIG. 2).

Example 4

Production of a Neuro2a Derived from Neuroblastoma into which an Ah Receptor Gene Expression Vector pcDNA4-rAhR, a Receptor Responsive Reporter Vector pTHEn-Luc-Zeocin and a β-Galactosidase Gene Expression Vector pcDNA4/V5-His/LucZ are Introduced A Lipofectamine 2000 (manufactured by Invitrogen Corporation) was used for the transfection of the Ah receptor gene expression vector pcDNA4-rAhR, receptor responsive reporter vector and β-galactosidase gene expression vector pcDNA4/V5-His/LucZ into Neuro2a. Neuro2a was subcultured on a 24-well plate by 80% confluent ($8 \times 10^4$ cells) and cultured in a DF 1:1 medium containing 10% fetal bovine serum. 2 μL of Lipofectamine 2000 was mixed with a 50 μL Opti-MEM medium (manufactured by Gibco Co., Ltd.) and this medium was left still at room temperature for 15 minutes. After that, the obtained medium was sufficiently mixed with a 50 μL Opti-MEM medium containing 0.2 μg of a receptor gene expression vector pcDNA4-rAhR produced in Example 2, 0.2 μg of a β-galactosidase gene expression vector pcDNA4/V5-His/LucZ and 0.4 μg of a reporter vector pTHEn-Luc-Zeiocin. The pcDNA4-rAhR and pcDNA4/V5-His/LucZ were digested with MunI into a linear form prior to use. Further, the pTHEn-Luc-Zeocin was likewise digested with NotI into a linear form prior to use. A mixture solution containing Lipofectamine 2000 and three types of linear gene expression vectors was left still at room temperature for 20 minutes and was added to Neuro2a cultured in advance on a 24-well plate and the mixture was mixed gently. After cultured for 24 hours, Neuro2a was diluted to 1/50 with a fresh DF 1:1 medium containing 10% fetal bovine serum and subcultured on a 6-well plate, and the culturing was further continued. After Neuro2a was cultured for 24 hours, zeocin (manufactured by Invitrogen Corporation) was added at a concentration of 250 μg/mL to the medium to start the selection of a cell into which pcDNA4-rAhR, pcDNA4/V5-His/LucZ and pTHEn-Luc-Zeocin were introduced. Thereafter, the medium was replaced with a fresh medium containing 250 μg/mL every 3 to 4 days to continue culturing. After two weeks had passed, cloning rings (manufactured by Iwaki Co., Ltd.) were used to obtain 10 to 12 types of zeocin resistant cell colonies. The above series of operations was performed three times to obtain a total of 33 types of colonies. These cells were selected as cell lines stably carrying receptor expression nucleic acid pcDNA4-rAhR, pcDNA4/V5-His/LucZ and pTHEn-Luc-Zeocin.

Example 5

Comparison of the Number of Copies of a Receptor Responsive Reporter Vector pTHEn-Luc-Zeocin Between Clones by Southern Hybridization Method

[Production of Southern Blot]

A Z3 line less responsive to 2,3,7,8-TCDD among the recombinant cells produced based on the production method described in Example 4, and a N2a-SY1 line (also referred to as a Z12 line) and a N2a-SY2 line (also referred to as a Z7 line) which were recombinant cells according to the embodiment, were cultured in a DF 1:1 medium for 3 to 5 days and then, a genome DNA was extracted from each cell by using a DNeasy Tissue kit (manufactured by Qiagen). The obtained genome DNA, a receptor responsive reporter vector pTHEn-Luc-Zeocin as a positive control and a genome DNA as a negative control were each perfectly digested in an amount of 5 μg by NcoI+XbaI to react at 37° C. overnight in a 100 μL scale.

10 μL of a 3M sodium acetate solution and 750 μL of isopropanol were added to the resultant to precipitate genome DNA fragments generated by a reaction with a restriction enzyme. The obtained fragments were washed with 70% ethanol to dry up, and then, the precipitated DNA fragments were redissolved in 12 μL of TE.

3 μL of 6× dye was added to the solution, which was then spun down by a centrifuge, and a marker (1 kb rudder; manufactured by New England Biolabs) and a sample were applied to a 0.8% agarose gel to undergo electrophoresis at room temperature and a voltage of 50 V for about 2 hours. At this time, perfectly digested receptor responsive reporter vectors pTHEn-Luc-Zeocin corresponding to 1, 3, 10, 30 and 100 copies respectively were applied simultaneously as positive controls.

The obtained agarose gel was transferred to a tapper and immersed in 0.25 N hydrochloric acid, and the solution was then shaken gently for 10 minutes. After hydrochloric acid was removed and the gel was rinsed with distilled water, the gel was immersed in 0.4 N sodium hydroxide and the solution was further shaken gently for 10 minutes. By a capillary method using 0.4 N sodium hydroxide, Genome DNA fragments separated in the agarose gel was transferred to a nylon membrane (Hybond-XL; Amersham Biosciences) at room temperature overnight.

The nylon membrane to which the genome DNA fragments were transferred was immersed in 2×SSC, which was then gently shaken, followed by air drying and the resulting membrane was stored at room temperature before it was used for hybridization.

[Production of a Radioactive Probe, Hybridization, Washing, Autoradiography]

A receptor responsive reporter vector pTHEn-Luc-Zeocin was perfectly digested with NcoI+XbaI to prepare a DNA fragment (1.7 kbp) suitable for Southern hybridization.

Using a DNA labeling kit (Megaprime DNA Labelling System, manufactured by Amersham Biosciences), 25 to 50 ng of a probe DNA fragment was labeled by [$^{32}$P] dCTP (NEG-513Z, manufactured by Perkin Elmer) according to the random prime method. The [$^{32}$P] labeled DNA fragment was then purified by using a Sephadex spin column (ProveQuant G-50 Micro-Columns, manufactured by Amersham Biosciences).

After the radioactivity of the fragment was confirmed, the fragment was heated at 95° C. for 5 minutes and ice-cooled for 5 minutes just after heated, to denature, thereby obtaining a [$^{32}$P] labeled probe.

The nylon membrane to which a genome DNA fragment was transferred was placed in a hybridization buffer to pre-incubate at 65° C. for 1 hour, and then, the denatured [$^{32}$P] labeled probe was added to a 100 μL hybridization buffer to incubate at 65° C. for 4 hours.

After the incubation was finished, the nylon membrane was taken out and was subjected to middle-salt concentration washing (1×SSC, 0.1% SDS, at 65° C. for 1 hour) to confirm radioactivity derived from the probe bound with the membrane by a survey meter. When sufficient radioactivity was bound to the membrane, the membrane was subjected to low salt concentration washing (0.2×SSC, 0.1% SDS, at ambient temperature for about 5 minutes).

Figure 3:
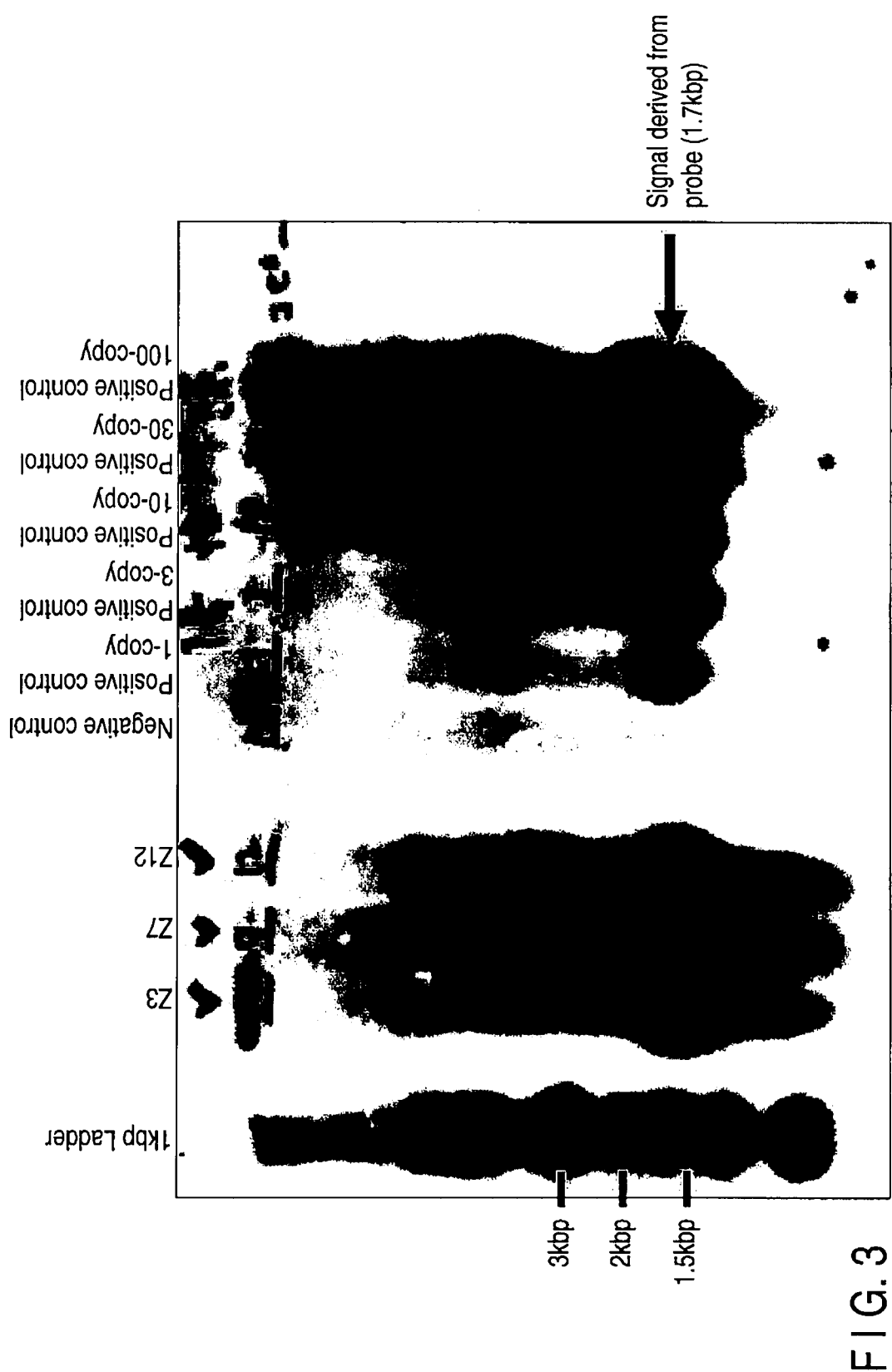
FIG. 3 shows the result of Southern hybridization showing the number of copies of an Ah receptor responsive reporter vector pTHEn-Luc-Zeocin carried by the recombinant cells.

The washed membrane was sealed with Saran Wrap (trademark), on which an X-ray film (BioMax MS, manufactured by Kodak Japan Ltd.) was then overlapped. The sealed membrane was then placed in an autoradiography cassette, which was then exposed to light at 4° C. for 3 days to one week and then the X-ray film was exposed to X-rays to detect specific signals derived from the hybridization with the [$^{32}$P] labeled probe. The results are shown in FIG. 3. The results shown in FIG. 3 are those obtained by performing Southern hybridization, and FIG. 3 shows the results of a 1 kbp ladder, Z3 line, Z7 line, Z12 line, negative control, 1-copy positive control, 3-copy positive control, 10-copy positive control, 30 copy positive control and 100-copy positive control from the left side thereof. No signal was observed in the case of a negative control, whereas a stronger signal was observed with the increase in the number of copies in the case of a positive control.

From the results of the analysis, it was confirmed that the N2a-SY1 line and N2a-SY2 line cells which were the recombinant cells of the embodiment retained a higher number of copies of the receptor responsive reporter vector pTHEn-Luc-Zeocin than the Z3 line which was a low-responsive clone.

Figure 4:
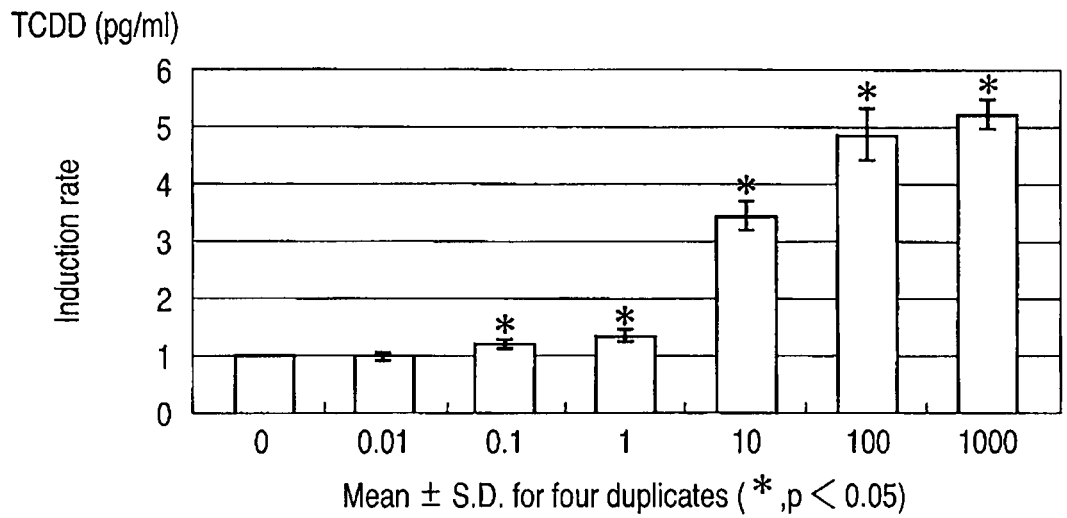
FIG. 4 is a graph showing the result of measurement of the transcriptional activation potency of 2,3,7,8-TCDD by using the recombinant cells.

These N2a-SY1 line and N2a-SY2 line cells were internationally deposited with National Institute of Advanced Industrial Science and Technology International Patent Organism Depositary as of Aug. 5, 2009. These N2a-SY1 line and N2a-SY2 line cells are the cells deposited as FERM BP-11165 and FERM BP-11166, respectively.

nm. Using a standard curve, the absorbance was converted into the amount of β-galactosidase (ng) in the protein extract. The results are shown by a bar graph in FIG. 4, and also in Table 1 showing each value (in the table, each value is a compensated value calculated by dividing the luminescence relative light units (RLU) of luciferase by the absorbance of β-galactosidase and bB/A means the magnification of activation [signal-to-noise ratio]).

TABLE 1

Compensated value and signal-to-noise ratio, calculated by dividing the luminescence relative light units (RLU) for luciferase obtained on the measurement of the transcriptional activation function of 2,3,7,8-TCDD in the recombinant cell, by absorbance of β-galactosidase

|  | 0 (pg/ml) | 0.01 (pg/ml) | 0.1 (pg/ml) | 1 (pg/ml) | 10 (pg/ml) | 100 (pg/ml) | 1000 (pg/ml) |
|---|---|---|---|---|---|---|---|
| N2a-SY1 (LUC)[a] | 1177.3 | 1187.8 | 1451.5 | 1577.6 | 4029.7 | 5718.5 | 6132.5 |
| N2a-SY1 (magnification of activation)[b] | 1 | 1. | 1.24 | 1.34 | 3.43 | 4.88 | 5.22 |

Example 6

Measurement of the Transcriptional Activation Potency of 2,3,7,8-TCDD by Using the Recombinant Cells of the Embodiment The recombinant cells (N2a-SY1) produced in Example 4 were seeded on a 24-well plate with about 80,000 cells per well and then cultured in a DE 1:1 medium of 10% serum for several hours to overnight.

Next, the medium of the recombinant cell cultured in the above manner was aspirated to remove it, and DF 1:1 mediums of 10% serum which contained a 2,3,7,8-TCDD in concentrations of 0, 0.1, 1, 10, 100 and 1000 pg/mL, respectively were each dispensed in each well with 1 mL per well to culture cells. The culturing of cells was continued, the medium was removed after 24 hours and the cells were washed once with PBS 1 mL per well. Then, 200 μL per well of a PicaGene Cell Culture Lysis Reagent Luβ (manufactured by Toyo B-Net Co., Ltd.) diluted five times was added to each well, which was then allowed to stand at room temperature for 10 minutes or more to dissolve, thereby obtaining a cell extract. The obtained cell extract was frozen-stored in a freezing chamber, this frozen-stored plate was taken out of the freezing chamber, and the cell extract was fused at room temperature. 10 μL of the fused cell extract was transferred to a black 96-well plate. Then, 100 μL per well of a PicaGene (trademark) LT210 luminescence substrate solution was dispensed in each well of the plate and mixed and then, the plate was set to a Mithras LB940 Microplate Reader (manufactured by Berthold Japan K.K.) to measure a luminescence amount continuously. Separately, 10 μL of the above cell extract was transferred to a transparent 96-well plate. 150 μL of a β-galactosidase substrate solution (ONPG substrate solution) was added to each well of the plate, which was incubated at room temperature for 5 minutes, and then, 50 μL of a reaction stop solution (aqueous 1 mM sodium carbonate solution) was added to each well. Then, the plate was set to a micro-plate reader to measure absorbance of each well at 405

Example 7

Measurement of the Transcriptional Activation Potency of PCB126 by Using the Recombinant Cell of the Embodiment The stable recombinant cells (N2a-SY1) produced in Example 4 were seeded on a 24-well plate with about 80,000 cells per well and cultured in a DF 1:1 medium of 10% serum for several hours to overnight.

Figure 5:
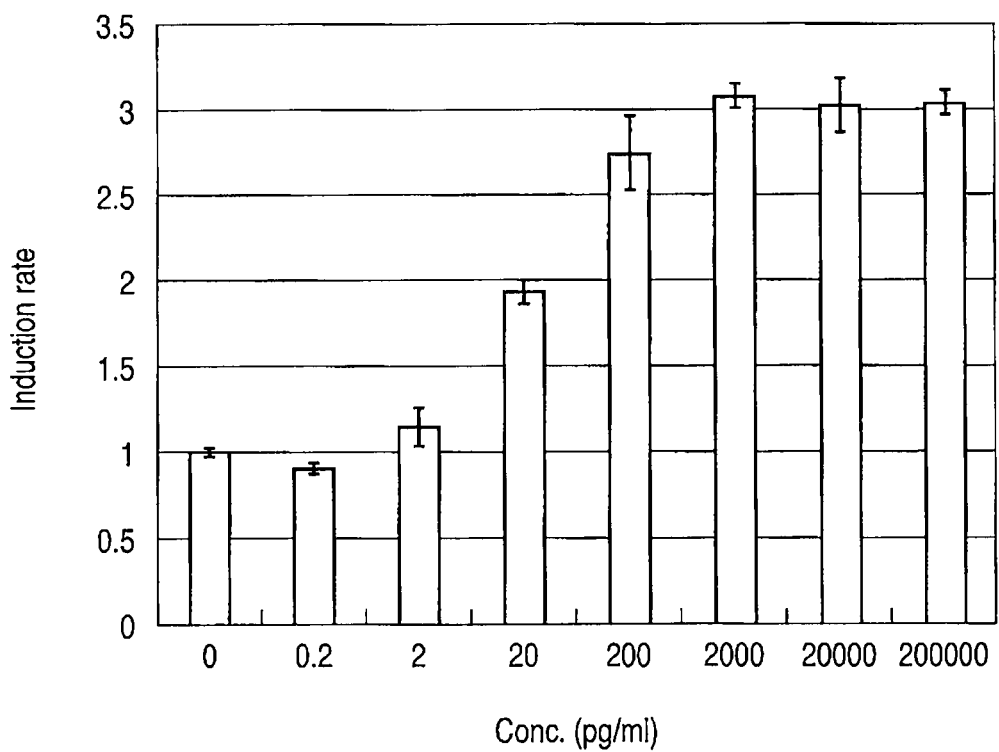
FIG. 5 is a graph showing the results of measurement of transcriptional activation potency of PCB126 by using the recombinant cells.

Next, the medium of the recombinant cell cultured in the above manner was aspirated to remove it, and DF 1:1 mediums of 10% serum which contained PCB126 at concentrations of 0, 0.2, 2, 20, 200, 2000, and 20000 pg/mL respectively were dispensed in each well with 1 mL per well to culture cells. The culturing of cells was continued, the medium was removed after 24 hours and the cells were washed once with PBS 1 mL per well. Then, 200 μL per well of a PicaGene Cell Culture Lysis Reagent Luβ (manufactured by Toyo B-Net Co., Ltd.) diluted five times was added to each well, which was then allowed to stand at room temperature for 10 minutes or more to dissolve, thereby obtaining a cell extract. The obtained cell extract was frozen-stored in a freezing chamber, this frozen-stored plate was taken out of the freezing chamber, and the cell extract was fused at room temperature. 10 μL of the fused cell extract was transferred to a black 96-well plate. Then, 100 μL per well of a PicaGene (trademark) LT210 luminescence substrate solution was dispensed in each well of the plate and mixed and then, the plate was set to a Mithras LB940 Microplate Reader (manufactured by Berthold Japan K.K.) to measure a luminescence amount continuously. Separately, 10 μL of the above cell extract was transferred to a transparent 96-well plate. 150 μL of a β-galactosidase substrate solution (ONPG substrate solution) (manufactured by Sigma-Aldrich Corporation) was added to each well of the plate, which was incubated at room temperature for 5 minutes, and then, 50 μL of a reaction stop solution (aqueous 1 mM sodium carbonate solution) was added to each well. Then, the plate was set to a micro-plate reader to measure absorbance of each well at 405 nm. Using a standard curve, the absorbance was converted into the amount of β-galactosidase (ng) in the protein extract. The results are shown by a bar graph in FIG. 5, and also in Table 2 showing each value (in the table, each value is a compensated value calculated by dividing the luminescence relative light units (RLU) of luciferase by the absorbance of β-galactosidase and [b]B/A means the magnification activation [signal-to-noise ratio]).

TABLE 2

Compensated value and signal-to-noise ratio, calculated by dividing the luminescence relative light units (RLU) for luciferase obtained on the measurement of the transcriptional activation function of PCB126 in the recombinant cell by β-galactosidase

|  | 0 (pg/ml) | 0.2 (pg/ml) | 2 (pg/ml) | 20 (pg/ml) | 200 (pg/ml) | 2000 (pg/ml) | 20000 (pg/ml) | 200000 (pg/ml) |
|---|---|---|---|---|---|---|---|---|
| N2a-SY1 (LUC)[a] | 2075.4 | 1882.6 | 2388 | 3991 | 5685.8 | 6401.6 | 6264.8 | 6268.9 |
| N2a-SY1 (magnification of activation)[b] | 1 | 0.91 | 1.15 | 1.92 | 2.74 | 3.08 | 3.02 | 3.02 |

Example 8

Measurement of the Transcriptional Activation Potency of KC400 by Using the Recombinant Cell of the Embodiment The stable recombinant cells (N2a-SY1) produced in Example 4 were seeded on a 24-well plate with about 80,000 cells per well and cultured in a DF 1:1 medium of 10% serum for several hours to overnight.

Figure 6:
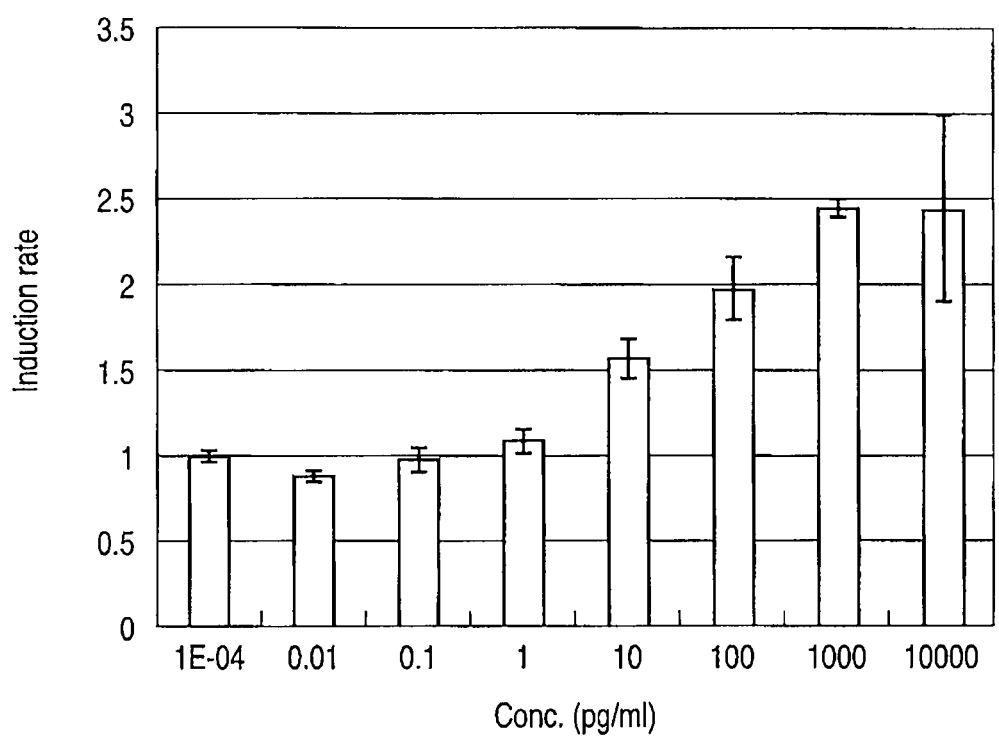
FIG. 6 is a graph showing the results of measurement of transcriptional activation potency of KC400 by using the recombinant cells.

Next, the medium of the recombinant cell cultured in the above manner was aspirated to remove it, and DF 1:1 mediums of 10% serum which contained KC400 at concentrations of 1E-04, 0.01, 0.1, 1, 10, 100, 1000, and 10000 ng/mL, respectively were dispensed in each well with 1 mL per well to culture cells. The culturing of cells was continued, the medium was removed after 24 hours and the cells were washed once with PBS 1 mL per well. Then, 200 μL per well of a PicaGene Cell Culture Lysis Reagent Luβ (manufactured by Toyo B-Net Co., Ltd.) diluted five times was added to each well, which was then allowed to stand at ambient temperature for 10 minutes or more to dissolve, thereby obtaining a cell extract. The obtained cell extract was frozen-stored in a freezing chamber, this frozen-stored plate was taken out of the freezing chamber, and the cell extract was fused at room temperature. 10 μL of the fused cell extract was transferred to a black 96-well plate. Then, 100 μL per well of a PicaGene (trademark) LT210 luminescence substrate solution was dispensed in each well and mixed and then, the plate was set to a Mithras LB940 Microplate Reader (manufactured by Berthold Japan K.K.) to measure a luminescence amount continuously. Separately, 10 μL of the above cell extract was transferred to a transparent 96-well plate. 150 μL of a β-galactosidase substrate solution (ONPG substrate solution) (manufactured by Sigma-Aldrich Corporation) was added to each well of the plate, which was incubated at room temperature for 5 minutes, and then, 50 μL of a reaction stop solution (aqueous 1 mM sodium carbonate solution) was added to each well. Then, the plate was set to a micro-plate reader to measure absorbance of each well at 405 nm. Using a standard curve, the absorbance was converted into the amount of β-galactosidase (ng) in the protein extract. The results are shown by a bar graph in FIG. 6, and also in Table 3 showing each value (in the table, each value is a compensated value calculated by dividing the luminescence relative light units (RLU) of luciferase by the absorbance of β-galactosidase and [b]B/A means the magnification of activation [signal-to-noise ratio]).

TABLE 3

Compensated value and signal-to-noise ratio, calculated by dividing the luminescence relative light units (RLU) for luciferase obtained on the measurement of the transcriptional activation function of KC400 in the recombinant cell, by β-galactosidase

|  | 1E-04 (pg/ml) | 0.01 (pg/ml) | 0.1 (pg/ml) | 1 (pg/ml) | 10 (pg/ml) | 100 (pg/ml) | 1000 (pg/ml) | 10000 (pg/ml) |
|---|---|---|---|---|---|---|---|---|
| N2a-SY1 (LUC)[a] | 3483.3 | 3167.3 | 3425.9 | 3759.2 | 5441.9 | 6844.1 | 8539.5 | 8519.9 |
| N2a-SY1 (magnification of activation)[b] | 1 | 0.91 | 0.98 | 1.08 | 1.56 | 1.96 | 2.45 | 2.44 |

Accession No.
FERM BP-11165
FERM BP-11166

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A cell having an Accession No. FERM BP-11165 or FERM BP-11166.

2. A method for assaying an aryl hydrocarbon receptor transcriptional activation potency of a test substance, comprising:
   (1) contacting the test substance with the cell according to claim 1;
   (2) obtaining an amount of a translation product of the reporter gene or an indication value having a correlation to the amount of the translation product in the cell which has been brought into contact with the test substance; and
   (3) assaying the aryl hydrocarbon receptor transcriptional activation potency of the test substance based on the amount of the translation product of the reporter gene or the indication value obtained in (2).

3. The method according to claim 2, wherein the contacting between the cell and the test substance in (1) is maintained for 20 hours or more.

4. An assay kit comprising the cell according to claim 1, wherein the assay kit is suitable for measuring a level of aryl hydrocarbon receptor transcriptional activation.

5. A method for selecting or exploring a material having an aryl hydrocarbon receptor transcriptional activation potency, comprising:
   selecting a material having an aryl hydrocarbon receptor transcriptional activation potency based on the aryl hydrocarbon receptor transcriptional activation potency assayed by the method according to claim 2.

6. The cell according to claim 1, having an Accession No. FERM BP-11165.

7. The cell according to claim 1, having an Accession No. FERM BP-11166.

* * * * *

SEQUENCE LISTING

<160> NUMBER OF SEQ ID NOS: 15

<210> SEQ ID NO 1
<211> LENGTH: 539
<212> TYPE: DNA
<213> ORGANISM: Artificial
<220> FEATURE:
<223> OTHER INFORMATION: AhR binding enhancer, and promoter of TH gene

<400> SEQUENCE: 1

```
tagatctaat tgcatccact tcgcaggcac ctcctctgaa tcaccctccg ccctagacac      60
gacatgaaga ctgcatccac tgtcgcaggc acctgcctct gaatcaccct ccgccctaga     120
cacgacatga agacaggggc tggcgccagc ccctgtcttc atgtcgtgtc tagggcggag     180
ggtgattcag aggcaggtgc ctgcgacagt ggatgcagtc ttcatgtcgt gtctagggcg     240
gagggtgatt cagaggaggt gcctgcgaca gtggatgcaa ttagatctag ccagcccctg     300
tcttcatgtc gtgtctaggg cggagggtga ttcagaggca ggtgcctgcg acagtggatg     360
cagtcttcat gtcgtgtcta gggcggaggg tgattcagag gcaggtgcct gcgacagtgg     420
atgcaattag atctagggct cgaggtgggg gacccagagg ggctttgacg tcagcctggc     480
ctttaagagg ccgcctgcct ggcaagggct gtggagacag aactcgggac caccagctt     539
```

<210> SEQ ID NO 2
<211> LENGTH: 435
<212> TYPE: DNA
<213> ORGANISM: Artificial
<220> FEATURE:
<223> OTHER INFORMATION: TH gene enhancer region

<400> SEQUENCE: 2

```
tagatctaat tgcatccact tcgcaggcac ctcctctgaa tcaccctccg ccctagacac      60
gacatgaaga ctgcatccac tgtcgcaggc acctgcctct gaatcaccct ccgccctaga     120
cacgacatga agacaggggc tggcgccagc ccctgtcttc atgtcgtgtc tagggcggag     180
ggtgattcag aggcaggtgc ctgcgacagt ggatgcagtc ttcatgtcgt gtctagggcg     240
gagggtgatt cagaggaggt gcctgcgaca gtggatgcaa ttagatctag ccagcccctg     300
tcttcatgtc gtgtctaggg cggagggtga ttcagaggca ggtgcctgcg acagtggatg     360
cagtcttcat gtcgtgtcta gggcggaggg tgattcagag gcaggtgcct gcgacagtgg     420
atgcaattag atcta                                                     435
```

<210> SEQ ID NO 3
<211> LENGTH: 24
<212> TYPE: DNA
<213> ORGANISM: Mus musculus
<220> FEATURE:
<223> OTHER INFORMATION: AhR binding enhancer sequence located in 5'
    upstream region of TH gene cording region

<400> SEQUENCE: 3

```
gtcttcatgt cgtgtctagg gcgg                                            24
```

<210> SEQ ID NO 4
<211> LENGTH: 95
<212> TYPE: DNA
<213> ORGANISM: Artificial
<220> FEATURE:
<223> OTHER INFORMATION: Promoter of TH gene

<400> SEQUENCE: 4

```
gtgggggacc cagagggggct tgacgtcag cctggccttt aagaggccgc ctgcctggca    60
agggctgtgg agacagaact cgggaccacc agctt                               95

<210> SEQ ID NO 5
<211> LENGTH: 93
<212> TYPE: DNA
<213> ORGANISM: Simian virus 40
<220> FEATURE:
<223> OTHER INFORMATION: Simian virus 40 early promoter

<400> SEQUENCE: 5
atttatgcag aggccgaggc cgcctcggcc tctgagctat tccagaagta gtgaggaggc    60 tttttttggag gcctaggctt ttgcaaaaag ctt                                93

<210> SEQ ID NO 6
<211> LENGTH: 165
<212> TYPE: DNA
<213> ORGANISM: Simian virus 40
<220> FEATURE:
<223> OTHER INFORMATION: Simian virus 40 late promoter

<400> SEQUENCE: 6
ggtgtggaaa gtccccaggc tccccagcag gcagaagtat gcaaagcatg catctcaatt    60
agtcagcaac caggtgtgga aagtcccag gctcccagc aggcagaagt atgcaaagca    120
tgcatctcaa ttagtcagca accatagtcc cgcccctaac tccgc                  165

<210> SEQ ID NO 7
<211> LENGTH: 758
<212> TYPE: DNA
<213> ORGANISM: human herpesvirus 1
<220> FEATURE:
<223> OTHER INFORMATION: Human herpesvirus 1 thymidine kinase promoter

<400> SEQUENCE: 7
gatctaaatg agtcttcgga cctcgcgggg gccgcttaag cggtggttag ggtttgtctg    60
acgcgggggg aggggggaagg aacgaaacac tctcattcgg aggcggctcg ggtttggtc   120 ttggtggcca cgggcacgca gaagagcgcc gcgatcctct taagcacccc cccgccctcc   180
gtggaggcgg gggtttggtc ggcgggtggt aactggcggg ccgctgactc gggcgggtcg   240
cgcgccccag agtgtgacct tttcggtctg ctcgcagacc cccgggcggc ccgccgcgg   300 cggcgacggg ctcgctgggt cctaggctcc atggggaccg tatacgtgga caggctctgg   360
agcatccgca cgactgcggt gatattaccg gagaccttct gcgggacgag ccgggtcacg   420
cggctgacgc ggagcgtccg ttgggcgaca acaccagga cggggcacag gtacactatc   480
ttgtcacccg gaggcgcgag ggactgcagg agcttcaggg agtggcgcag ctgcttcatc   540
cccgtggccc gttgctcgcg tttgctggcg gtgtccccgg aagaaatata tttgcatgtc   600
tttagttcta tgatgacaca aaccccgccc agcgtcttgt cattggcgaa ttcgaacacg   660
cagatgcagt cggggcggcg cggtcccagg tccacttcgc atattaaggt gacgcgtgtg   720
gcctcgaaca ccgagcgacc ctgcagcgac ccgcttaa                          758

<210> SEQ ID NO 8
<211> LENGTH: 1836
<212> TYPE: DNA
<213> ORGANISM: cytomegalovirus
<220> FEATURE:
<223> OTHER INFORMATION: Cytomegalovirus early enhancer/promoter

<400> SEQUENCE: 8
```

```
agatctaaat gagtcttcgg acctcgcggg ggccgcttaa gcggtggtta gggtttgtct      60
gacgcggggg gagggggaag gaacgaaaca ctctcattcg gaggcggctc ggggtttggt     120
cttggtggcc acgggcacgc agaagagcgc cgcgatcctc ttaagcaccc ccccgccctc     180
cgtggaggcg ggggtttggt cggcgggtgg taactggcgg gccgctgact cgggcgggtc     240
gcgcgcccca gagtgtgacc ttttcggtct gctcgcagac ccccgggcgg cgccgccgcg     300
gcggcgacgg gctcgctggg tcctaggctc catggggacc gtatacgtgg acaggctctg     360
gagcatccgc acgactgcgg tgatattacc ggagaccttc tgcgggacga gccgggtcac     420
gcggctgacg cggagcgtcc gttgggcgac aaacaccagg acggggcaca ggtacactat     480
cttgtcaccc ggaggcgcga gggactgcag gagcttcagg gagtggcgca gctgcttcat     540
ccccgtggcc cgttgctcgc gtttgctggc ggtgtccccg gaagaaatat atttgcatgt     600
ctttagttct atgatgacac aaaccccgcc cagcgtcttg tcattggcga attcgaacac     660
gcagatgcag tcgggcggc gcggtcccag gtccacttcg catattaagg tgacgcgtgt     720
ggcctcgaac accgagcgac cctgcagcga cccgcttaaa agcttgattc ttctgacaca     780
acagtctcga acttaagctg cagaagttgg tcgtgaggca ctgggcaggt aagtatcaag     840
gttacaagac aggtttaagg agaccaatag aaactgggct tgtcgagaca gagaagactc     900
ttgcgtttct gataggcacc tattggtctt actgacatcc actttgcctt tctctccaca     960
ggtgtccact cccagttcaa ttacagctct taaggctaga gtacttaata cgactcacta    1020
taggctagcc accatgactt cgaaagttta tgatccagaa caaggaaac ggatgataac     1080
tggtccgcag tggtgggcca gatgtaaaca aatgaatgtt cttgattcat ttattaatta    1140
ttatgattca gaaaaacatg cagaaaatgc tgttattttt ttacatggta acgcggcctc    1200
ttcttattta tggcgacatg ttgtgccaca tattgagcca gtagcgcggt gtattatacc    1260
agacctatt ggtatgggca atcaggcaa atctggtaat ggttcttata ggttacttga     1320
tcattacaaa tatcttactg catggtttga acttcttaat ttaccaagaa agatcatttt    1380
tgtcggccat gattgggggtg cttgtttggc atttcattat agctatgagc atcaagataa    1440
gatcaaagca atagttcacg ctgaaagtgt agtagatgtg attgaatcat gggatgaatg    1500
gcctgatatt gaagaagata ttgcgttgat caaatctgaa gaaggagaaa aaatggtttt    1560
ggagaataac ttcttcgtgg aaaccatgtt gccatcaaaa atcatgagaa agttagaacc    1620
agaagaattt gcagcatatc ttgaaccatt caaagagaaa ggtgaagttc gtcgtccaac    1680
attatcatgg cctcgtgaaa tcccgttagt aaaaggtggt aaacctgacg ttgtacaaat    1740
tgttaggaat tataatgctt atctacgtgc aagtgatgat ttaccaaaaa tgtttattga    1800
atcggaccca ggattctttt ccaatgctat tgttga                              1836
```

<210> SEQ ID NO 9
<211> LENGTH: 34
<212> TYPE: DNA
<213> ORGANISM: artificial
<220> FEATURE:
<223> OTHER INFORMATION: primer

<400> SEQUENCE: 9
cccaagctta ccatgagcag cggcgccaac atca                                   34

<210> SEQ ID NO 10
<211> LENGTH: 34
<212> TYPE: DNA
<213> ORGANISM: artificial

```
<220> FEATURE:
<223> OTHER INFORMATION: primer

<400> SEQUENCE: 10
ccgctcgaga ggaatccgct gggtgtgata tcag                              34

<210> SEQ ID NO 11
<211> LENGTH: 145
<212> TYPE: DNA
<213> ORGANISM: artificial
<220> FEATURE:
<223> OTHER INFORMATION: template for PCR amplification

<400> SEQUENCE: 11
gccagcccct gtcttcatgt cgtgtctagg gcggagggtg attcagaggc agtgcctgcg    60
acagtggatg cagtcttcat gtcgtgtcta gggcggaggg tgattcagag gcaggtgcct   120
gcgacagtgg atgcaattag atcta                                        145

<210> SEQ ID NO 12
<211> LENGTH: 16
<212> TYPE: DNA
<213> ORGANISM: artificial
<220> FEATURE:
<223> OTHER INFORMATION: primer

<400> SEQUENCE: 12
gccagcccct gtcttc                                                   16

<210> SEQ ID NO 13
<211> LENGTH: 16
<212> TYPE: DNA
<213> ORGANISM: artificial
<220> FEATURE:
<223> OTHER INFORMATION: primer

<400> SEQUENCE: 13
tagatctaat tgcatc                                                   16

<210> SEQ ID NO 14
<211> LENGTH: 34
<212> TYPE: DNA
<213> ORGANISM: artificial
<220> FEATURE:
<223> OTHER INFORMATION: primer

<400> SEQUENCE: 14
cggagcgctc ctaggctttt gcaaaaagct cccg                               34

<210> SEQ ID NO 15
<211> LENGTH: 34
<212> TYPE: DNA
<213> ORGANISM: artificial
<220> FEATURE:
<223> OTHER INFORMATION: primer

<400> SEQUENCE: 15
gctcgcgacg gtatacagac atgataagat acat                               34
```